United States Patent [19]
Rosenthal et al.

[11] Patent Number: 5,319,200
[45] Date of Patent: Jun. 7, 1994

[54] RAPID NEAR-INFRARED MEASUREMENT OF NONHOMOGENEOUS SAMPLES

[75] Inventors: Todd C. Rosenthal; Daniel Kaminsky, both of Hagerstown; Robert D. Rosenthal, Gaithersburg, all of Md.

[73] Assignee: Zeltex, Inc., Hagerstown, Md.

[21] Appl. No.: 890,163

[22] Filed: May 29, 1992

Related U.S. Application Data

[63] Continuation-in-part of Ser. No. 710,895, Jun. 5, 1991, abandoned.

[51] Int. Cl.$^5$ .............................................. G01N 21/35
[52] U.S. Cl. ...................................... 250/341; 250/343; 250/349; 250/339.01
[58] Field of Search ................. 250/341, 227.23, 359.1, 250/339, 343, 349, 227.28, 227.11; 356/432

[56] References Cited

U.S. PATENT DOCUMENTS

| | | |
|---|---|---|
| 3,286,327 | 11/1966 | Ganci . |
| 3,806,730 | 4/1974 | Tirkkonen et al. ................. 250/341 |
| 4,379,238 | 4/1983 | Minakuchi .......................... 307/243 |
| 4,404,462 | 9/1983 | Murray ............................... 219/497 |
| 4,466,076 | 8/1984 | Rosenthal .......................... 356/418 |
| 4,692,620 | 9/1987 | Rosenthal .......................... 250/343 |
| 4,973,561 | 11/1990 | Hansen et al. ..................... 250/343 |
| 5,019,710 | 5/1991 | Wennerberg et al. .............. 250/341 |

FOREIGN PATENT DOCUMENTS

| | | | |
|---|---|---|---|
| 2416465 | 8/1979 | France | 356/432 |
| 2078938 | 1/1982 | United Kingdom | 356/432 |

OTHER PUBLICATIONS

Graf, "Radio Shack Dictionary of Electronics", Howard Sams & Co., 1978, pp. 402-405.

*Primary Examiner*—Carolyn E. Fields
*Attorney, Agent, or Firm*—Rothwell, Figg, Ernst & Kurz

[57] ABSTRACT

A rapid near-infrared instrument for measuring constituents of nonhomogeneous samples is disclosed which alleviates the need for taking successive measurements of the sample, and repositioning the sample for each successive measurement, by providing a novel illumination system including a light pipe which transmits near-infrared energy to the sample at a plurality of substantially separate and independent location. This arrangement permits a plurality of subsample measurements to be taken simultaneously which enables accurate constituent measurements to be made quickly and easily.

12 Claims, 4 Drawing Sheets

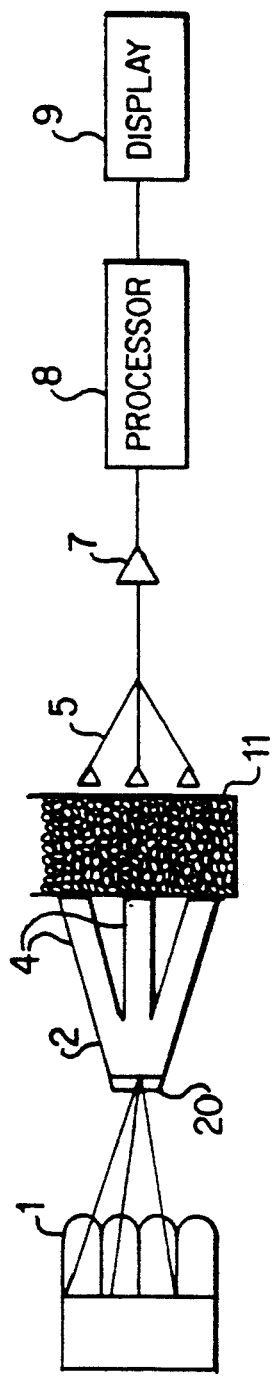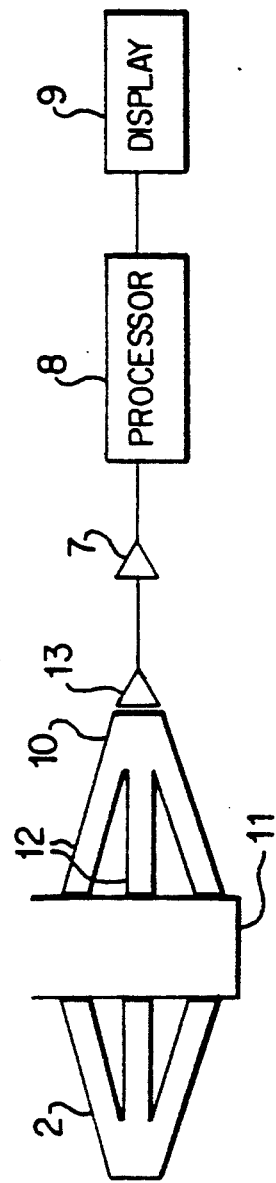

RAPID NEAR-INFRARED MEASUREMENT OF NONHOMOGENEOUS SAMPLES

CROSS-REFERENCE TO RELATED APPLICATION

This application is a continuation-in-part of prior co-pending application Ser. No. 710,895, filed Jun. 5, 1991, now abandoned.

BACKGROUND OF THE INVENTION

1. Field of the Invention

This invention relates to methods and instrumentation for nondestructively measuring constituents, such as protein, moisture and oil in nonhomogeneous samples using near-infrared radiation, and particularly the rapid near-infrared measurement of such nonhomogeneous samples. More particularly, this invention provides an easy to use, low-cost instrument for analyzing constituents of nonhomogeneous samples, such as grain samples.

2. Description of the Prior Art

Near infrared measuring instruments that provide an accurate measure of constituents, such as protein, moisture and oil in nonhomogeneous organic products and other products utilizing near-infrared radiation are known in the art and have become commercially successful. Such instruments are particularly useful for measuring protein, oil and moisture in cereal grain in a totally nondestructive mode to a high degree of accuracy. Such instruments are commercially available from Trebor Industries, Inc. in Gaithersburg, Md. For example, in the grain industry, thousands of country elevators are currently using the TREBOR-90XL to provide protein and moisture measurements in wheat and barley. Similarly, in the food industry, the TREBOR-99 and the TREBOR-30A instruments are widely used in the near-infrared analysis of snack food, candy products, etc. These instruments are described in U.S. Pat. Nos. 3,286,327, 4,379,238, 4,404,462, 4,466,076 and 4,692,620, each assigned to Trebor Industries, Inc.

Although these known instruments have proven to be commercially successful, they, nevertheless, do have certain limitations. One such limitation is that these known devices require successive measurements from multiple locations, so that the resultant constituent measurements represent a meaningful average of the total product. Taking these multiple successive measurements of a single nonhomogeneous sample can result in larger time consumption and additional mechanical complexity. Specifically, the prior art devices require the nonhomogeneous sample to be moved, then stopped, in front of the near-infrared source and detector, and measurements made. The sample to be analyzed must then be again moved, stopped and measured wherein this process is repeated several times. In general, this process has to be done approximately 10 to 20 times in order to provide acceptable accuracy and precision. The process of repeatedly stopping, moving and measuring a single nonhomogeneous sample to obtain its constituent measurements can be burdensome and time consuming, typically lasting thirty seconds or longer. (See U.S. Pat. No. 4,692,620).

Further, accomplishing these multiple starts and stops requires the use of mechanical components which have an inherent lower reliability and add to the instrument's overall complexity.

While a number of prior art devices have proposed fiber optic containing assemblies for transmitting energy from a source to a sample, the use of fiber optics will lead to undue expense in the cost of manufacture. While fiber optics have many unique characteristics, we have found these characteristics to be unnecessary in the present application of near-infrared analytical technology.

Thus, there is a great need for an accurate, reliable near-infrared instrument having increased sample measuring speed and which is not subject to the mechanical "weakness" and complexity inherent in the current generation of instruments. Further, there is a need for an inexpensive analytical instrument which does not employ fiber optic technology in the interest of maintaining costs to manufacture at a minimum.

SUMMARY OF THE INVENTION

Accordingly, the present invention provides a near-infrared instrument for rapidly measuring the constituents of a nonhomogeneous sample including an energy source for directing infrared-energy toward a sample to be analyzed and means for transmitting the near-infrared energy to the sample at a plurality of substantially separate and independent locations. The present invention further includes a detector means for detecting the near-infrared energy transmitted through sample at the substantially separate and independent locations and which produces a signal related to the near-infrared energy received thereby. The signal from the detector means is processed by a microprocessor to provide a quantitative measurement of the constituents of the sample to be analyzed and is displayed.

Simultaneously transmitting near-infrared energy to substantially separate and independent portions of the nonhomogeneous sample according to the present invention produces an effective measurement of several sub-samples and thus a meaningful average of the total sample to be analyzed. The present invention alleviates the need to move the sample.

In one preferred embodiment, the inventive apparatus includes a multi-node light pipe means for simultaneously transmitting the near-infrared energy to selected portions of the sample. In another preferred embodiment, the apparatus further includes a second multi-node light pipe means for simultaneously collecting the near-infrared energy which has interacted with selected portions of the sample.

BRIEF DESCRIPTION OF THE DRAWINGS

FIG. 1 is a side view of a rapid near-infrared instrument for the measurement of nonhomogeneous samples according to the present invention;

FIG. 2 is a side view of an illumination system according to a second embodiment of the present invention;

DETAILED DESCRIPTION OF THE PREFERRED EMBODIMENT

The rapid near-infrared instrument for the measurement of nonhomogeneous samples will be discussed in detail with reference to FIG. 1 which shows a source means 1 for transmitting near-infrared energy toward a nonhomogeneous sample, i.e. such as wheat, contained in a sample holding means 11. The source means 1 is used to generate a near-infrared spectra and can be any suitable energy source such as the Infrared Emitting Diode ("IRED") system shown in FIG. 1.

Figure 3A:
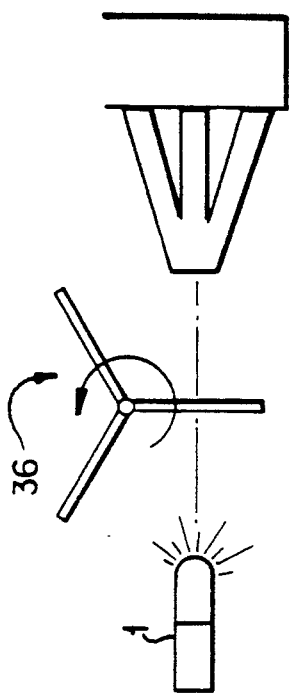
FIGS. 3A–D show schematic views of different near-infrared energy sources that can be used with the illumination system of the present invention.
Figure 3B:
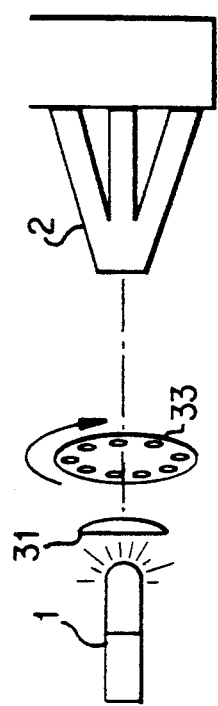
Figure 3C:
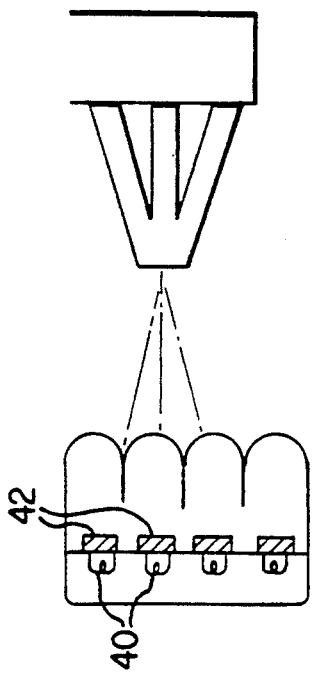
Figure 3D:
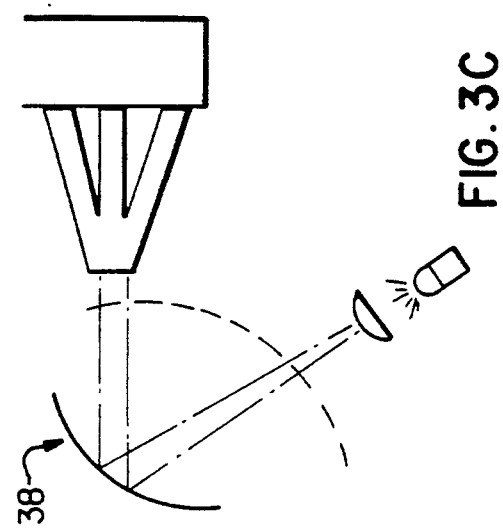

FIGS. 3A-D illustrates several different types of near-infrared sources that can be in the present invention. FIG. 3A and 3B show mechanically rotating narrow bandpass filter systems which utilize a filter wheel and tilting filter, respectively. In FIG. 3A, near-infrared energy from light source 1 passes through a focussing lens 31, a filter on filter wheel 33 and on to light pipe 2. The rotating filter assembly is seen in FIG. 3B, designated by reference numeral 36. FIG. 3C shows a prism or grating system designated by reference numeral 38. FIG. 3D shows in greater detail a novel IRED module, shown in FIG. 1, which can hold as many as 16 IREDs and more. IRED chips 40 have narrow bandpass filters 42 disposed in the light path emanating therefrom.

A near-infrared radiation transmission means 2 is positioned to receive near-infrared radiation from the source means 1 and is used to subdivide the near-infrared energy into a number of separate branches. In a preferred embodiment shown in FIG. 1, the transmission means 2 is a multi-node light pipe assembly having a plurality of branches 4 for illuminating substantially separate and independent portions of the nonhomogeneous sample. The light pipe assembly is randomized so that each of the branches 4 receives the same spectra as is being entered into the base of the light pipe from the source means 1. In the preferred embodiment, the base of the light pipe is positioned near the focal point of the source means 1.

If a light source which produces a relatively columnar or "pin-point" emission is employed, it may be advantageous to provide a diffusion means 20 over the base of the light pipe. Any known light-diffusing material, e.g., a panel of frosted glass or acrylic, can be affixed to the base of the light pipe, preferably contiguous therewith. Alternatively, the base itself can be provided with a light-diffusing surface treatment, such as by chemical or physical etching.

Light pipe 2 can be manufactured of any material which is capable of transmitting near-infrared energy with a minimum of loss. A preferred version of the light pipe 2 is molded in a single piece from a transparent acrylic or polycarbonate polymer, and has nine branches for transmitting near-infrared energy to nine separate portions of the non-homogeneous sample. Unlike fiber optic cables, the branches 4 of the light pipe are substantially rigid. Such rigidity avoids the need to constantly adjust the position of the individual ends of the branches for optimum performance of the apparatus.

Although the light pipe assembly in FIG. 1 shows only three branches 4, any suitable number of branches can be used which will enable measurement of a meaningful average of the total sample to be analyzed. Again, in a preferred embodiment, the array will be arrayed in a matrix of 3×3 branches, or a matrix of 4×4 branches. Any suitable number or combination thereof can be used as discussed above.

The near-infrared energy from source means 1 and the transmission means 2 is transmitted into the nonhomogeneous sample which is contained in a sample holding means 11 which has at least a portion of a walls thereof being transparent to near-infrared radiation. The sample holding means 11 can be any container suitable for holding a sample to be analyzed such as wheat. The sides of the holder means are made of any suitable material, such as glass, which is transparent to near-infrared energy at least in the wavelengths between 600 nm and 1100 nm.

As illustrated in FIG. 1, the sample holding means 3 is located substantially adjacent to the near-infrared transmission light pipe means 2 which enables the near-infrared radiation to illuminate a plurality of substantially separate and individual portions of the sample. In the preferred embodiment, the light pipe branches 4 illuminate substantially separate independent portions of the sample. The distance between the branches 4 are chosen to insure that one branch provides a measurement point essentially independent to any other branch. This arrangement will result in obtaining measurements from several sub-samples with no significant interference from any adjacent branch.

The near-infrared radiation transmitted through the sample from the plurality of separate and independent portions is received and detected by detector means. The detector means in one embodiment comprises an array of individual silicon detectors 5 which are located opposite each branch of the light pipe. Each detector produces an electrical signal related to the infrared energy received thereby. The electrical signal from each detector 5 is summed using standard technology (not shown) and is then amplified by amplifier 7. The amplified signal from the sum of all detectors 4 is processed by processing means 8 to provide a quantitative measurement of the constituents of the sample to be analyzed. The signal from the detectors is processed by processing means 8 substantially as set out in U.S. Pat. Nos. 4,286,327, 4,379,238 and 4,404,462, incorporated herein by reference. Information processed in the signal processor 8 is displayed on a display 9.

Although the detector array of FIG. 1 shows only three detector elements, any suitable number of detectors can be used. In one embodiment, the detector array will comprise an array arrangement of nine detectors located in a 3×3 matrix, or a 4×4 matrix, or any combination thereof. Preferably, the total number and location of the detectors will correspond to the number and location of the light pipe branches 4 being used.

FIG. 2 illustrates novel illumination and detection means according to a second embodiment of the present invention including the near-infrared transmission means 2, as shown in FIG. 1, and a second multi-node light pipe 10 facing the transmission means 2. In this embodiment, the second light pipe 10 has a plurality of branches 12 and is positioned such that its branches receive near-infrared radiation transmitted through the sample from the branches 4. Near-infrared radiation received from the branches 12 is channeled toward the base of the light pipe array and is detected by a single detector 13. This embodiment eliminates multiple detectors and summing circuitry and is therefor somewhat less complicated and less expensive to manufacture than the apparatus depicted in FIG. 1. The signal from detector 13 is amplified by amplifier 7 and processed in microprocessor 8 as described above with reference to embodiment shown in FIG. 1.

Figure 4:
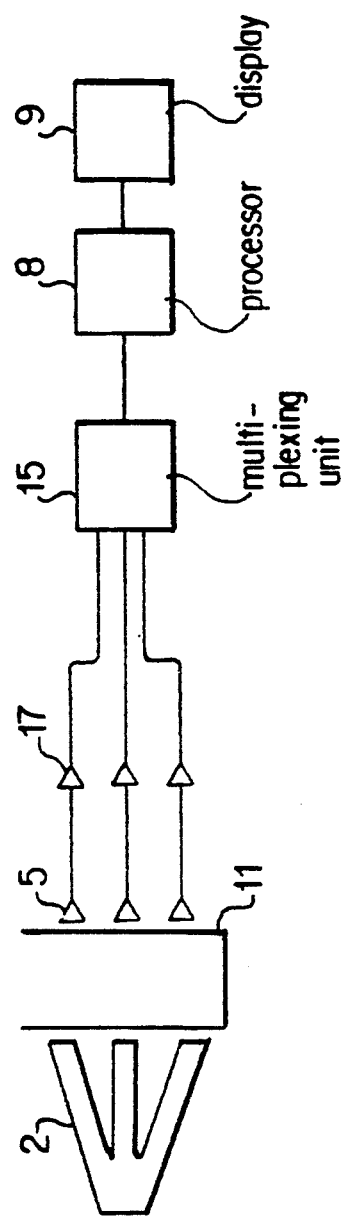
FIG. 4 is a side view of an illumination system according to another embodiment of the present invention which can be used in the rapid near-infrared measurement instrument shown in FIG. 1.

FIG. 4 illustrates a novel illumination and detection means according to a preferred embodiment of the present invention wherein the electrical signal from each detector 5 is amplified by a separate amplifier 17 and is input into a multiplexing unit 15. Each signal input into the multiplexing unit 15 is integrated by the microprocessor 8 and is individually input into microprocessor 8. The results of the independent measurements are averaged in microprocessor 8 which processes a quantitative measurement of the constituents of the sample to be analyzed.

Figure 5:
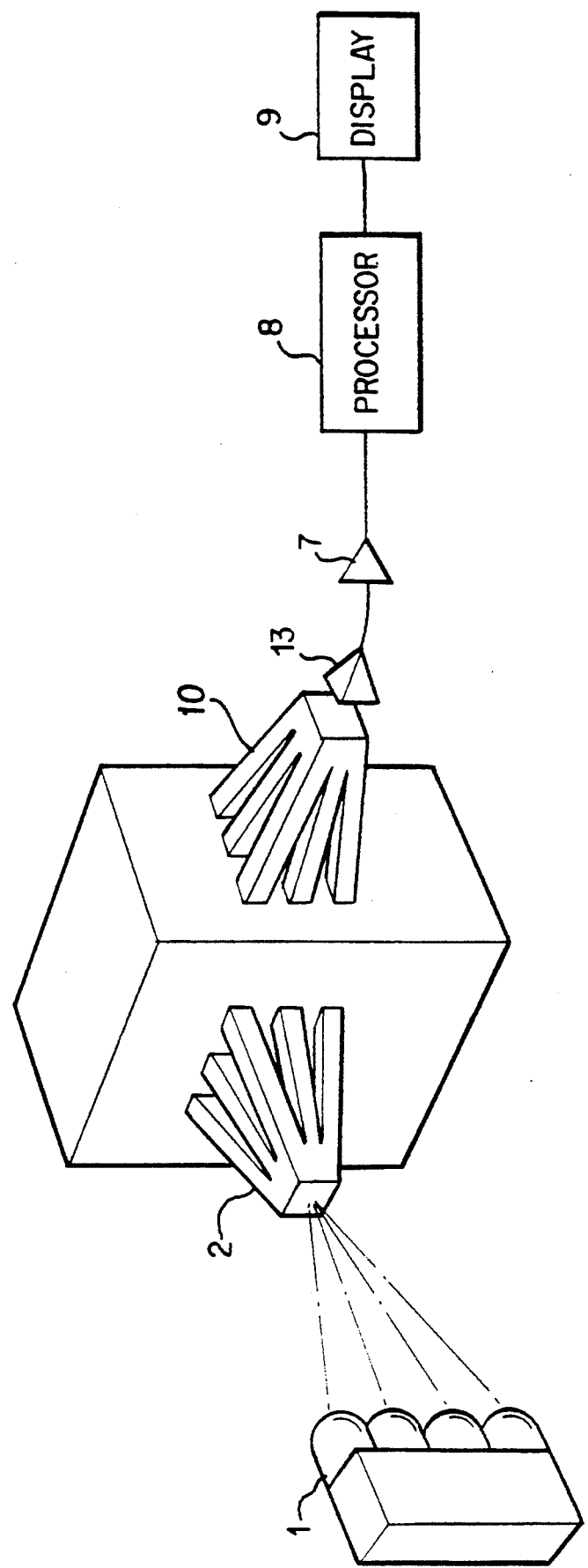
FIG. 5 is a side view of a rapid near-infrared instrument for the measurement of nonhomogeneous samples according to the present invention.

FIG. 5 illustrates a rapid near-infrared instrument according to still another embodiment of the present invention which utilizes the principle of nephelometry. In this embodiment, the measurement of the near-infrared radiation is made at a 90° angle to the incident near-infrared radiation. This approach avoids the possibility of grain-type products "bridging" and thus allowing light to directly transmit, through a hole between the sample particles, from the emitter to the detector. The energy received by branches 12 will be solely emitted from the sample. The embodiment illustrated in FIG. 5 utilizes the same elements shown and described in reference to FIG. 1 and operates in substantially the same manner. Further, this instrument can be used with either the array of detectors approach (FIG. 1) or the light pipe array and single detector (FIG. 2).

A rapid near-infrared instrument according to the present invention was tested and was found to provide accurate, reliable measurement of a constituent of the sample without moving the sample which resulted in a substantial time saving. The instrument used in the test program contained the following parts and components. The near-infrared illumination energy was provided by a standard TREBOR-90XL illumination board including an optical filter and Fresnel lens (Trebor Number 2113). The sample chamber was a TREBOR-99 standard sample cell (Parts Number 2629, 2630, 2636, 2736 and 2764). The instrument utilized an array of 12 detectors obtained from Hammamatsu, Part Number S2386-45K, which were connected in series. The detection circuitry, microprocessor and display was provided from the standard TREBOR-90XL instrument. In accordance with a preferred embodiment, the outputs of each detector were separately amplified and inputted into a multiplexing unit and processed. Measurements obtained from the sample were accurate and were made in significantly less time than required by the prior art devices.

Although the invention has been described in connection with certain embodiments, it is not limited to them. Modifications within the scope of the following claims will be apparent to those skilled in the art without derogating the scope of the applicants' novel contribution to the art.

What is claimed is:

1. A rapid near-infrared measuring instrument for measuring one or more constituents of a sample to be analyzed, said instrument comprising:
   (a) means for holding a sample to be analyzed including at least a portion of a wall thereof being transparent to near-infrared energy;
   (b) source means for generating near-infrared energy;
   (c) transmission means for transmitting near-infrared energy from said source means and for illuminating a plurality of substantially separate, independent portions of said sample, said transmission means comprising a monolithic multi-node light pipe having a base portion and a plurality of rigid branches in optical connection with the base portion;
   (d) detector means for receiving and detecting near-infrared energy transmitted through said sample from said plurality of substantially separate, independent portions of said sample, said detector means producing a signal related to the infrared energy received thereby; and
   (e) means for processing said signal and providing a quantitative measurement of the constituents of said sample to be analyzed.

2. The rapid near-infrared measurement instrument according to claim 1, wherein said multi-node light pipe is molded and has said rigid light-pipe branches disposed in an array.

3. The rapid near-infrared measurement instrument according to claim 2 wherein said array comprises between approximately 2 and 20 light pipe branches.

4. The rapid near-infrared measurement instrument according to claim 2, wherein said array of light pipe branches is a matrix of $3 \times 3$ or $4 \times 4$ branches.

5. The rapid near-infrared measurement instrument according to claim 1, wherein said detector means comprises a plurality of detectors positioned to receive near-infrared energy transmitted from said sample from said separate and independent portions.

6. The rapid near-infrared measurement instrument according to claim 1, wherein said detector means further comprises a multi-node light pipe having a base portion and a plurality of rigid branches in optical connection with the base portion for receiving near-infrared energy transmitted from said sample and transmitting the received energy to a detector element disposed adjacent the base portion of the detector means.

7. The rapid near-infrared instrument according to claim 6, wherein said plurality of light pipe branches comprises an array of detector branches, each detector branch being disposed in a position so as to collect near-infrared energy transmitted into the sample from a corresponding branch of the transmission means.

8. The rapid near-infrared instrument according to claim 7, wherein said detector branches is a $3 \times 3$ or $4 \times 4$ matrix of branches.

9. The rapid near-infrared instrument according to claim 1, wherein said detector means receives near-infrared energy transmitted from said sample at an angle of 90° to incident near-infrared energy.

10. The rapid near-infrared instrument according to claim 6, wherein said detector means receives near-infrared energy transmitted from said sample at an angle of 90° to incident near-infrared energy.

11. The rapid near-infrared instrument according to claim 1, wherein said source means comprises a mechanically rotatable narrow band pass filter system.

12. The rapid near-infrared instrument according to claim 1, wherein said source means comprises a matrix of infrared emitting diodes.

* * * * *